US010226542B2

(12) United States Patent
Messina et al.

(10) Patent No.: US 10,226,542 B2
(45) Date of Patent: Mar. 12, 2019

(54) DEVICE FOR THE STERILIZATION OF STETHOSCOPES

(71) Applicant: Egohealth S.r.l., Siena (IT)

(72) Inventors: Gabriele Messina, Siena (IT); Sandra Burgassi, Siena (IT); Valerio Montagnani, Siena (IT); Daniele Messina, Siena (IT); Gabriele Cevenini, Siena (IT)

(73) Assignee: Egohealth S.r.l., Siena (IT)

( * ) Notice: Subject to any disclaimer, the term of this patent is extended or adjusted under 35 U.S.C. 154(b) by 128 days.

(21) Appl. No.: 15/322,834

(22) PCT Filed: May 29, 2015

(86) PCT No.: PCT/IB2015/054075
§ 371 (c)(1),
(2) Date: Dec. 29, 2016

(87) PCT Pub. No.: WO2016/001776
PCT Pub. Date: Jan. 7, 2016

(65) Prior Publication Data
US 2018/0200396 A1  Jul. 19, 2018

(30) Foreign Application Priority Data

Jul. 4, 2014  (IT) .............................. MI2014A1221

(51) Int. Cl.
*A61L 2/10*  (2006.01)
*A61L 2/24*  (2006.01)

(52) U.S. Cl.
CPC .................. *A61L 2/10* (2013.01); *A61L 2/24* (2013.01); *A61L 2202/11* (2013.01);
(Continued)

(58) Field of Classification Search
CPC .......... A61L 2/10; A61L 2/24; A61L 2202/14; A61B 7/02
(Continued)

(56) References Cited

U.S. PATENT DOCUMENTS 9,918,803 B2 *  3/2018  Russ ........................ A61B 7/00
2005/0254992 A1 * 11/2005  Jenkins ..................... A61L 2/10
422/24

(Continued)

FOREIGN PATENT DOCUMENTS

| KR | 2009 0075136 A | 7/2009 |
|----|----------------|--------|
| KR | 10-0911729 B1  | 8/2009 |
| KR | 10-1324463 B1  | 10/2013 |

*Primary Examiner* — David A Vanore
(74) *Attorney, Agent, or Firm* — Blank Rome LLP

(57) ABSTRACT

This invention relates to a device for sanitising of medical instruments, in particular stethoscopes. In particular, this invention relates to a sanitisation or sterilisation device (1) for a stethoscope (S) comprising a case (2) that accommodates sanitisation or sterilisation means (3, 3', 3"), a command and control unit (4) and a battery (5), said device (1) comprising means for coupling to the stethoscope (S) to be sanitised or sterilised, said coupling means being magnetic or electromagnetic coupling means (12), mechanical coupling means (13) or a combination of them, characterised in that said case (2) presents to the outside a recess which forms an inverted cone (11), the base of which is open and substantially at the level of the outer surface of the case (2), said sanitisation or sterilisation means (3, 3', 3") being arranged in correspondence to said cone (11).

23 Claims, 6 Drawing Sheets

(52) U.S. Cl.
CPC ... *A61L 2202/122* (2013.01); *A61L 2202/123* (2013.01); *A61L 2202/14* (2013.01); *A61L 2202/24* (2013.01)

(58) Field of Classification Search
USPC .......................... 134/6; 250/455.11; 422/24
See application file for complete search history.

(56) References Cited

U.S. PATENT DOCUMENTS

| | | | | |
|---|---|---|---|---|
| 2009/0026237 | A1* | 1/2009 | Weaver | A45F 5/02 224/269 |
| 2015/0128997 | A1* | 5/2015 | Lesic | A61B 90/80 134/6 |
| 2016/0324996 | A1* | 11/2016 | Bilenko | A61L 2/10 |
| 2018/0078330 | A1* | 3/2018 | Russ | A61L 2/24 |

* cited by examiner

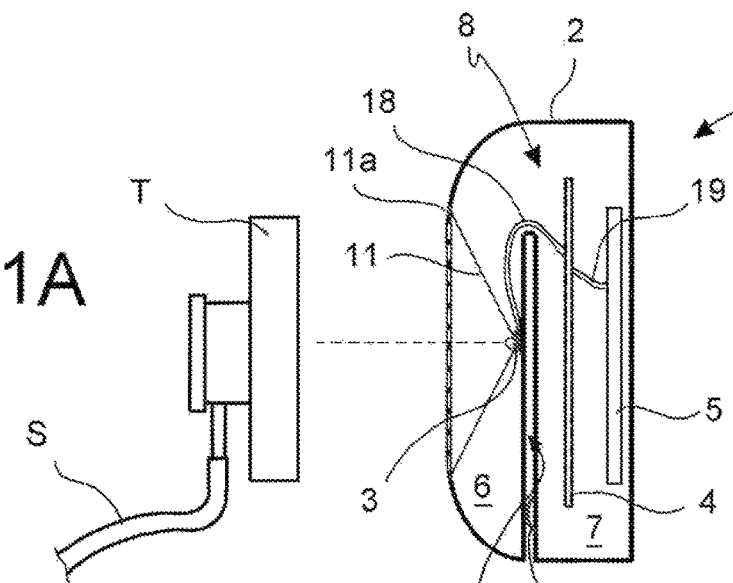
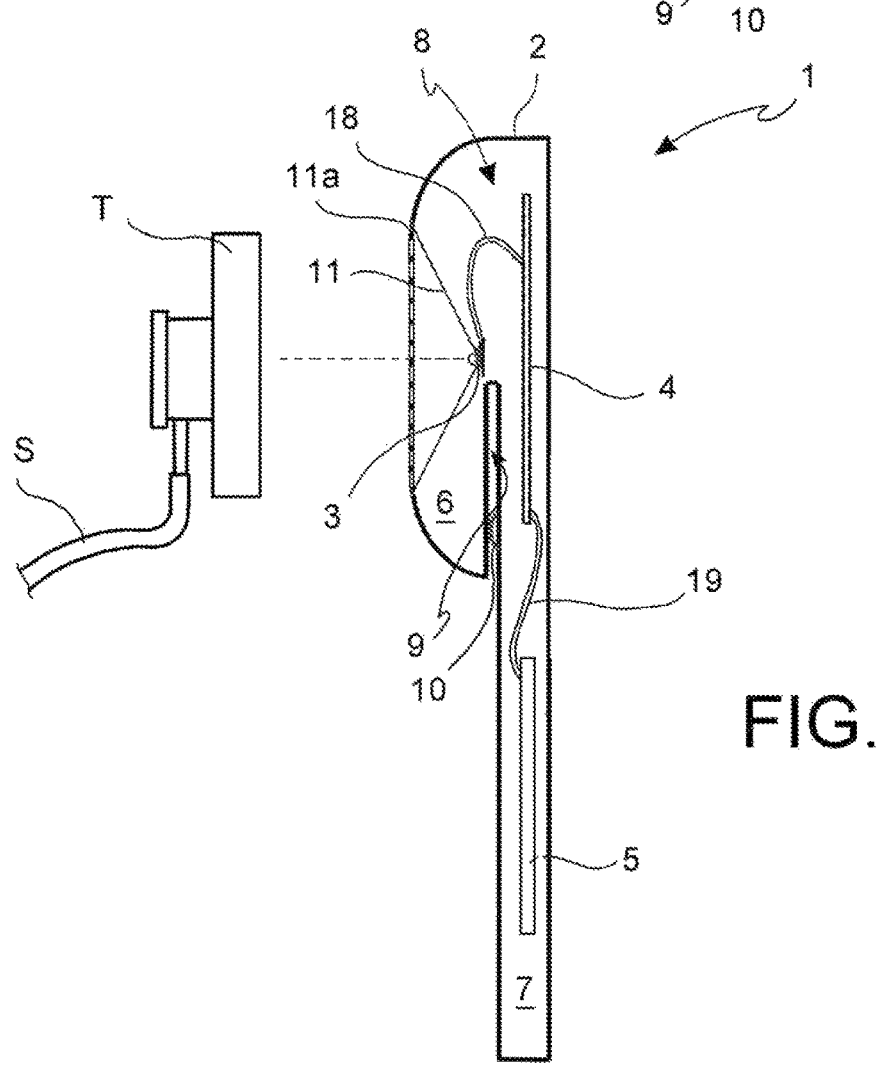

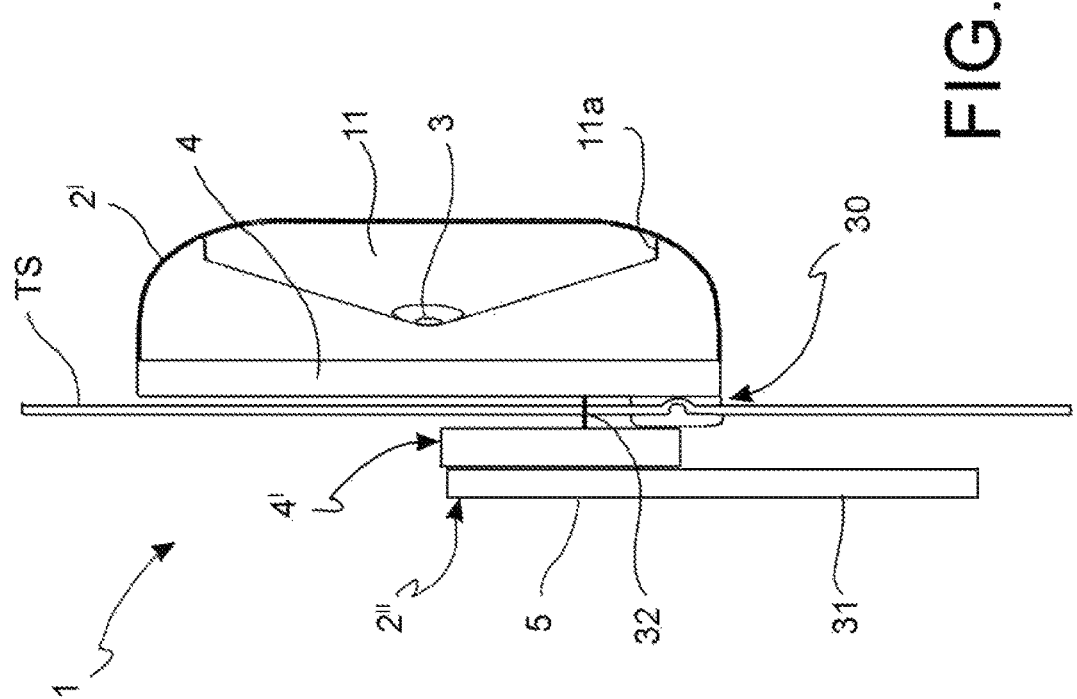
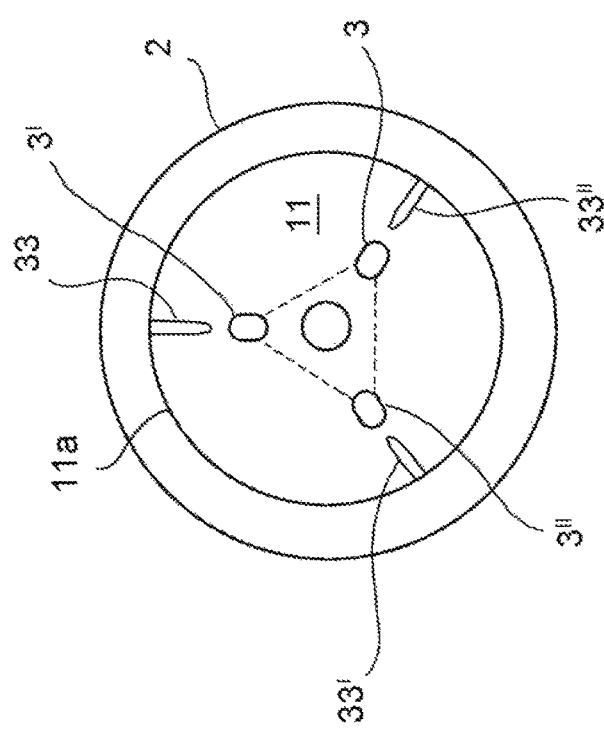

US 10,226,542 B2

DEVICE FOR THE STERILIZATION OF STETHOSCOPES

This invention relates to a device for the sanitisation or sterilisation of medical instruments, in particular stethoscopes.

In clinical and outpatient practice, doctors and healthcare workers make extensive use of portable instruments, frequently used for the assessment of the main physiological functions of the patient, for treatment and also for communicating and recording clinical data.

The hygiene of such instruments is of fundamental importance since it is known that their lack of sterility entails health risks, often severe. In fact, a large percentage of infectious diseases is of iatrogenic origin, mainly related to the lack of hygiene. These diseases, in addition to, obviously, damaging the health of the patient, significantly increase clinical and healthcare costs.

The vast majority of portable instruments are disposable and, as such, are suitably enclosed in sealed sterile packages; these include needles, syringes, gauze, electrodes, etc.

Other, typically more expensive, instruments used by healthcare professionals, such as scalpels, forceps, surgical instruments, catheters, etc., are first sterilized each time in special machines, generally quite expensive, bulky and sophisticated, placed in specific environments well separated from the operating theatres.

However, there are varied instruments that are frequently and commonly used by the medical staff (first of all, doctors), such as stethoscopes, thermometers, sphygmomanometers, otorhinolaryngological retractors, ophthalmological frames and lenses, etc., whose sanitisation must necessarily be frequently repeated each time they are used on different persons.

Unfortunately, though the problem of cross-infection (from doctor to patient and from patient to patient via the non-disposable medical instrumentation) is widely known, clear and scientifically verified, and there is a wide perception of the great effectiveness of meticulous sanitisation of these instruments in preventing associated infections, unfortunately doctors and healthcare workers continue to pay scant attention to systematically sanitizing instruments between one patient and another. This is often due to practical reasons and priorities for medical action mainly aimed at treating the patient and promptly restoring his vital functions.

Among the instruments that are frequently and repeatedly used, and therefore potential vehicles of infection, the stethoscope is the most common, at high risk for transmission of infections of iatrogenic origin. The function of the stethoscope is, through contact between its head with the various parts of the patient, to detect sounds coming from the patient's organs so that they can be interpreted in order to determine physiological or pathological conditions.

The literature provides ample evidence that stethoscopes can be a vehicle of cross-infection between one patient and another. In fact, it is rare, although desirable, that a doctor disinfects his stethoscope after each examination.

A key cause of the failure to sanitise is the practical difficulty to achieve adequate sanitisation/sterilisation under the doctor's normal operating conditions. In fact, the stethoscope is an instrument that the doctor typically carries with him during his examinations, often moving from place to place, while, as mentioned, the sterilisation devices are normally bulky and are housed in special rooms. Therefore, even if the doctor disinfected it after each examination, it would, most of the time, be hasty, inadequate and, in any case, uncontrollable in terms of effectiveness and safety.

Therefore, it would be desirable to have sanitisation systems that are as simple, light, compact, portable, safe, reliable and effective as possible to protect healthcare workers and patients.

For sanitizing or sterilizing medical-healthcare instruments, both chemicals and approaches based on physical principles can be used. The latter, with respect to the former, are not affected by microbial resistance and do not generate it, since they do not create selection mechanisms, but are generally associated with cumbersome and expensive devices that are therefore typically dedicated to hospital use.

Among all physical systems, the use of UV rays is effective and proven. It has been demonstrated that UV rays have sure disinfectant power (lowering the microbial charge), especially in the range of wavelengths comprised between 255 and 280 nm, with an actual sterilizing effect (inactivation of the microbial charge) when the exposure time is long enough.

Sanitization devices based on the principle of irradiation with UV light have already been proposed. However, due to their bulk, inconvenience of use and complexity, or high cost, they do not constitute a real solution to the problem that has been described above.

An important parameter in the design of a device of this type is the safety of the operator and the patient, in particular to avoid skin and eye damage caused by UV rays. This problem as well has not been solved in an easy and economical way by state-of-the-art devices.

Another important factor is the amount of UV radiation that reaches the surface to be sanitized. High irradiation efficiency allows reducing treatment times and sanitizing the entire surface of the instrument homogeneously.

The purpose of this invention is to provide a device for the sanitisation or sterilisation of medical-healthcare instruments, in particular stethoscopes, that solves the problems described above, and thus: has a weight and compactness that make it truly portable; is simple, effective and safe to use; allows automatic sanitisation or sterilisation, even not operator-dependent, in a short enough time to allow the operator to repeat it after each use; is simple and economic to make.

This purpose is achieved by a device for the sanitisation or sterilisation of medical-healthcare instruments as outlined in the appended claims, whose definitions are an integral part of this description.

Further characteristics and advantages of this invention will be more apparent from the description of several embodiments, provided below as non-limiting examples, with reference to the following figures:

FIGS. 1A and 1B is a schematic side view in section of the sanitisation or sterilisation device of the invention;

FIG. 8 is a plan view of a detail of an embodiment of the invention;

FIG. 9 is a schematic view in section of a further embodiment of the invention;

Figure 2:
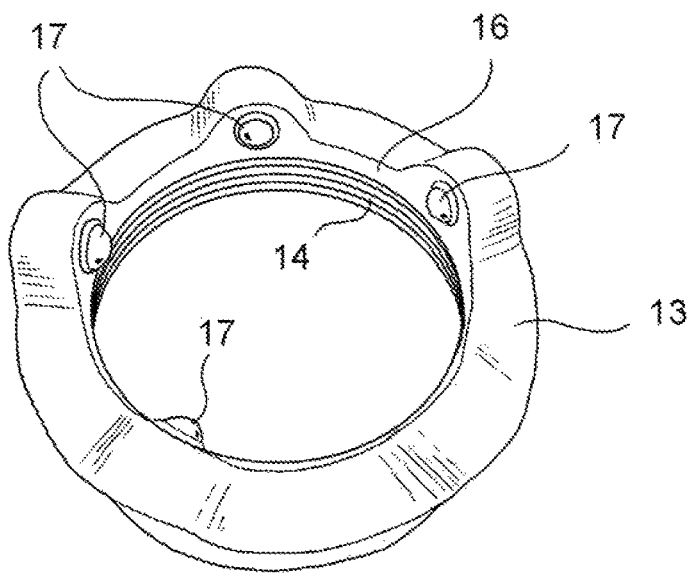
FIG. 2 is a top perspective view of an anchoring element associable to the device of FIGS. 1A and 1B.

The term "medical-healthcare instrument" refers to an instrument, or a non-disposable device, that has a surface that is intended to come into contact with the body of a human being, both for medical-healthcare reasons, as is the case for the instruments normally used by doctors and nurses, and for personal reasons, such as pacifiers and other objects used in infancy. In particular, the medical-healthcare instrument is a stethoscope.

With reference to the figures, reference number 1 indicates the sanitisation or sterilisation device according to the invention in its entirety.

The sanitisation or sterilisation device 1 comprises a case 2 that houses the sanitisation or sterilisation means 3, a command and control unit 4 and a battery 5.

The case 2 has a U-shaped cross-section, so as to comprise a first chamber 6 and second chamber 7 joined on one side by a connecting portion 8. In this way, between the two chambers and externally to them, a cavity 9 is formed in the shape of a slot that constitutes a means for attachment to a garment, for example the pocket of a white coat. To improve the attachment, one or more protuberances 10, fixed or sprung, are positioned on one of the two walls of the cavity 9.

In other embodiments, other attachment means may be provided to be positioned inside the cavity 9, for example pins, clasps, springs or tabs.

In still other embodiments, the case 2 may comprise a ring for the passage of a necklace, so as to hang the device on the neck of a user, or even a gripper to attach it to the collar or other part of the white coat or other garment.

In an embodiment (FIG. 1A), the first and the second chamber 6, 7 have substantially similar dimensions, so as to distribute the bulk and weight of the device uniformly between the two parts of the device, one intended to be positioned externally and the other internally with respect to the anchoring surface, for example the surface of a pocket.

In another embodiment (FIG. 1B), for a better stabilisation of the anchorage to the pocket of the white coat, and for a substantial reduction of the thickness of the chamber 7—intended to remain inside the pocket of the white coat—the chamber 7 can be longer than the chamber 6, extending downwards.

The outer case of chamber 7 can have various shapes with rounded or square corners, symmetrical or asymmetrical with respect to the position of the cone.

Figure 7:
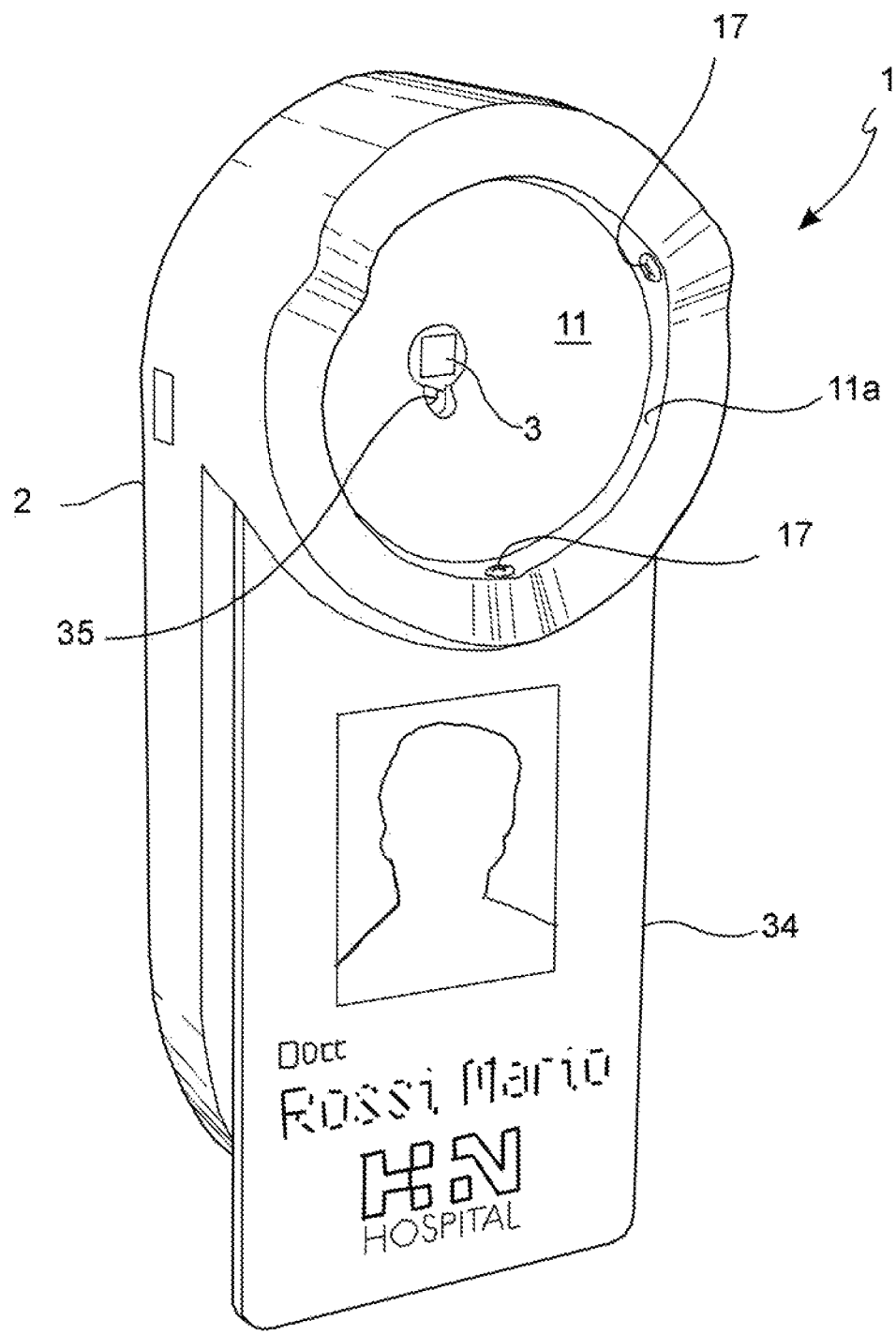
FIG. 7 is a perspective view of the device of the invention according to a different embodiment.

In a different embodiment, shown in FIG. 7, the chamber 6 may be provided externally with an extension constituted by a flat surface 34 that faces the outside of the white coat pocket, for example to contain advertising text, the operator's identifying data, a badge or other data of healthcare interest. This surface may also contain a small screen inserted in the badge.

In both of the two embodiments, the first chamber 6 presents to the outside a recess that forms an inverted cone 11, the base of which is open and at the level of the outer surface of the case 2, where it presents a base circumference 11*a* that constitutes an edge of the opening, while the apex has a seat in which are housed the sanitisation or sterilisation means 3.

The diameter of the base of the cone 11 is large enough to accommodate even larger stethoscopes.

In certain embodiments, the section along a vertical plane of the cone 11 has the oblique side with an inclination between 20° and 30° with respect to the base plane of the cone, so as to limit its height as much as possible and reduce as much as possible the distance between the sanitisation or sterilisation means 3 and the surface to be treated.

In certain embodiments, as shown in FIG. 8, from the base circumference 11*a* of the cone 11, thin, low ribs 33, 33', 33" with chamfered edges branch-off towards the centre of the cone 11. These ribs 33, 33', 33" have the function of creating support points for the head of the stethoscope, keeping it spaced from the cone 11 just enough to maximise the irradiated surface. In fact, by doing so, the irradiation of the light will better reach the lower circumference of the head of the stethoscope (membrane and its anchoring ring). The length of the ribs 33, 33', 33" is such as to allow the support of stethoscopes of various sizes.

In certain embodiments, the surface of the cone 11 facing the aperture is reflective. For example, gold or silver foil or plating may be provided. The conical shape and reflective properties of the surface of the cone 11 constitute a waveguide for UV-C rays. This allows a better directional guidance of the light and captures the light energy in a smaller volume, improving its effectiveness on the surface to be treated (membrane of the stethoscope). Furthermore, when the UV-C 3 LED is positioned at the centre of the cone 11, there is better protection of the sanitisation or sterilisation means 3, minimising the need to coat it with quartz or film transparent to the UV radiation.

As a reflective coating, certain embodiments may provide a titanium dioxide coating, in particular titanium dioxide in nanoparticle form that, in addition to having high reflective properties, in the presence of UV radiation performs a photocatalytic action that improves the sanitizing and antibacterial effect of the device.

The sanitisation or sterilisation means 3 are preferably means for the emission of UV-C radiation. More preferably, such means comprise one or more UV-C LEDs that emit radiation with a wavelength between 255 and 300 nm, and preferably about 280 nm.

Figures 4, 5, 6:
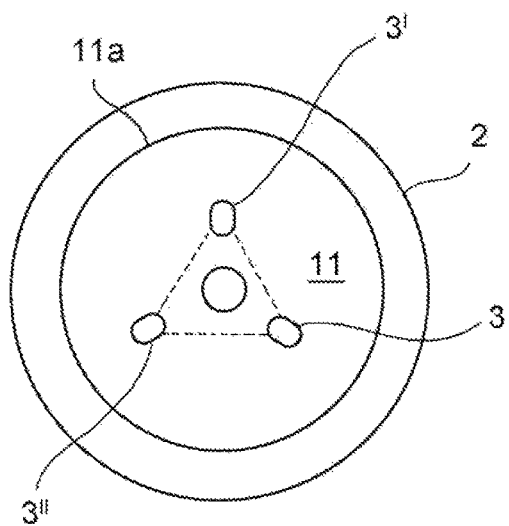
FIG. 4 is a top plan view of the device of the invention according to an embodiment.
FIG. 5 is a side view in section of a coupling member according to the invention.
FIG. 6 is a perspective view of the coupling member of FIG. 5 fixed to a stethoscope.

In a different embodiment of the invention, shown in FIG. 4, in which there are three UV-C 3 LEDs 3', 3", these are disposed along, and preferably inserted flush in, the walls of the cone 11 in a triangular configuration.

Preferably, the UV-C LEDs 3, 3', 3" have an irradiation angle between 120° and 140° and are placed in the configuration of an equilateral triangle along a circumference coaxial to the base circumference 11*a* of the cone 11 and whose projection on the base of the cone 11 is placed at a distance from the base circumference 11*a* of r/2 where r is the radius of the base circumference. In this way, total irradiation of the surface to be treated is obtained, reducing exposure times due to the shorter distance between the UV-C LEDs 3, 3', 3" and the surface to be treated.

In other embodiments (not shown), one can use just two UV-C LEDs, arranged, and preferably inserted flush, always along the walls of the cone 11 in opposing position. In this way, oval irradiation projections are created, suitable to best cover, compared to the single UV LED, the possible areas of side shadow, to strengthen the irradiation energy in the central areas of the cone 11 and to allow a multiplication of the UV-C rays going, in part, to irradiate the reflective surface of the cone 11 itself.

In still other embodiments, four or more UV-C LEDs may be used, arranged at the vertices of regular polygons.

The UV-C LEDs can be powered with direct current or, alternatively, using current waveforms to optimise light intensity and therefore maximise the biocidal effect. For example, one can use pulsing waveforms such as pulsed, triangular, square, sinusoidal, intermittent, etc., working at an appropriate frequency.

The device of the invention comprises means for coupling to the medical-healthcare instrument to be sanitized or sterilized. These coupling means may be magnetic coupling means, mechanical coupling means or a combination of them (magneto-mechanical means).

Figure 3:
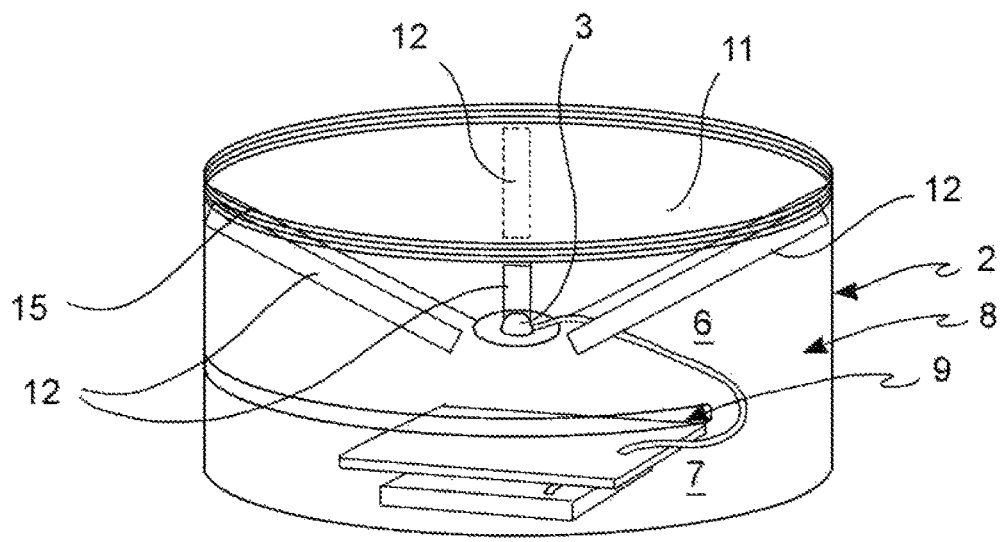
FIG. 3 is a side view in partial cross-section of the device of the invention according to an embodiment.

The magnetic coupling means consist of one or more permanent magnets 12 positioned on the inner surface of the first chamber 6 of the case 2, in correspondence to the cone 11. The magnets 12 may include a plurality of tabs arranged longitudinally on the inner wall of the cone 11 (as shown in FIG. 3), or one or more transverse tabs, or even a single magnetic element in the shape of a ring, coaxial with respect to the base circumference 11a of the cone 11. Obviously, the magnets 12 may assume any other shape and be in even or odd number and preferably be arranged at a regular distance from one another.

In certain embodiments, the permanent magnets 12 can be replaced by electromagnets.

The mechanical coupling means comprise a ring nut 13 (FIG. 2) that has an internal thread 14 that can be coupled with a threaded edge 15 (FIG. 3) provided in correspondence to the base circumference of the cone 11. In other embodiments (not shown), the thread 14 can instead be arranged externally. While, in other embodiments, the thread 14 of the ring nut 13 and the threaded edge 15 of the case 2 are replaced by a bayonet coupling system of conventional type.

Figure 10:
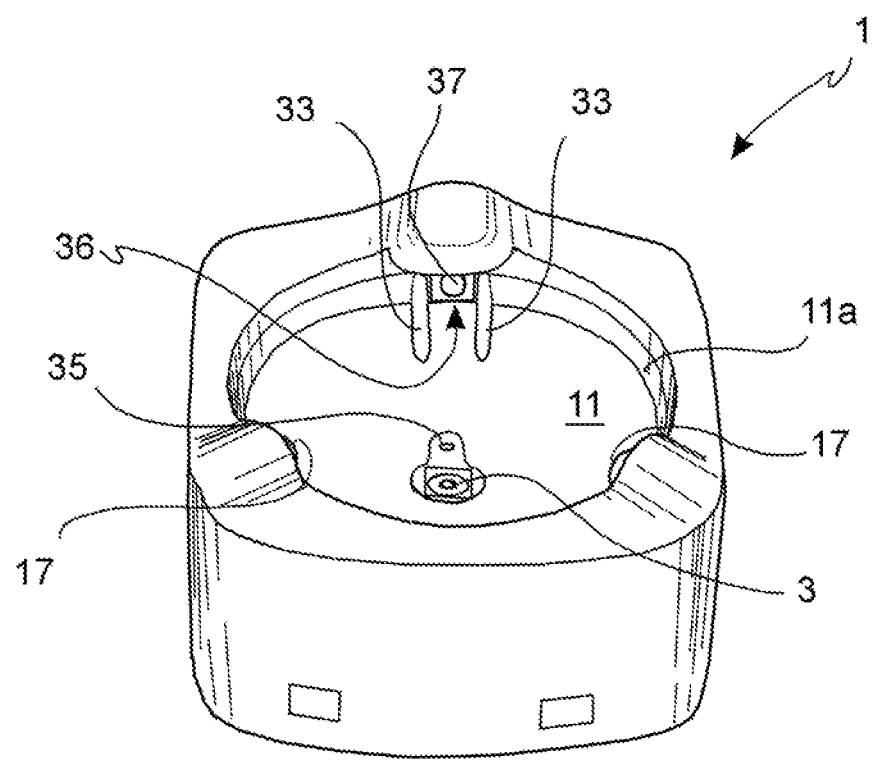
FIG. 10 is a perspective view of a different embodiment of the invention.

The ring nut 13 includes an inner surface 16 on which is disposed a plurality of engagement members 17, such as spring balls (shown in FIG. 2), the latch levers or similar and mechanical insertion niches. The engagement members may all be of the same type (homogeneous) or combined types. For example, as shown in FIG. 10, two spring balls and an insertion niche 36 so that the stethoscope is first slid under the niche 36 by appropriately tilting it, and then hooked by the engagement members (spring balls) 17. In each of these systems, it is possible to fix the head of the stethoscope to the ring nut 13 through the interaction of the edge of the stethoscope with the engagement members 17.

The insertion niche 36 is formed by a protuberance towards the inside of the outer edge of the cone 11, so as to create the space of the niche 36 below it.

In certain embodiments, permanent magnets in the shape of tabs, tiles or a continuous circle may be arranged within the body of the ring nut 13 or on its inner or outer surface. In this way, it will be possible to integrate the mechanical and magnetic couplings of the case 2 obtaining a more stable coupling.

The fact that the ring nut 13 is removable from the case 2 allows its use only in cases where it is not possible to associate a ferromagnetic element to the head of the stethoscope or when it is desired to use both the magnetic and mechanical couplings simultaneously.

Furthermore, the removability of the ring nut 13 allows using ring nuts 13 of different size, so as to adapt the device of the invention to stethoscopes of various types.

In other embodiments, the ring nut 13 will be integrally associated to the edge of the base circumference 11a of the cone 11.

In an embodiment (FIG. 1A), the second chamber 7 of the case 2 houses the command and control unit 4 and the battery 5. In this embodiment, the command and control unit 4 and the battery 5 are stacked.

In another embodiment (FIG. 1B), the second chamber 7 of the case 2 houses the command and control unit 4 and the battery 5 so that the command and control unit 4 and the battery 5 are arranged side by side on the same plane. This allows limiting the thickness of the chamber 7, intended to be accommodated in the pocket of an operator. In this case, the cavity 9 will preferably be shorter, remaining below the position of the LED.

The sanitisation or sterilisation means 3 are operatively connected to the command and control unit and the battery 5 via suitable cabling 18, 19, which is made to pass through the connecting portion 8 between the first chamber 6 and second chamber 7.

Various connection methods may be provided. A first possibility is that shown in the figures, in which the LED or LEDs 3, 3', 3" are connected to the command and control unit 4 via a first cable 18, while the command and control unit 4 is connected to the battery 5 via a second cable 19. In other embodiments, the cables 18, 19 directly connect the battery 5 to the LEDs 3, 3', 3" and command and control unit 4. In still other embodiments, a connection could be made between the LEDs 3, 3', 3" and the command and control unit 4 by means of suitable jacks.

The command and control unit 4 comprises a microprocessor or a microcontroller also with Digital Signal Processing (DSP) functions.

The command and control unit 4 performs the following functions:

a) controls that the device 1 is closed on the head T of the stethoscope S and sends a command of consent for the performance of steps b) and c);

b) commands and controls the powering on and off of the UV-C LEDs 3, 3', 3" based on the pre-set power-on times and power output;

c) checks for anomalies, such as a malfunction of the UV-C LED or LEDs 3, 3', 3" and an insufficient charge of the battery 5.

These operations are performed using conventional elements and logical that are full known to an expert in the field.

It is essential that step a) be performed first, so as to send the microprocessor a command of consent to step b).

Step c) can be performed at any time.

The closure control according to step a) is important in order to ensure safety for the operator and patient. In fact, if the UV-C LEDs 3, 3', 3" go into operation before the closure of the device, the UV-C radiation could be harmful for the health or the operator or the patient, especially if they reach the eyes or other sensitive parts of the body.

In certain embodiments, the control according to step a) is implemented by means of a contact or magnetic induction pressure and/or spring micro-switch 37 arranged in a suitable position along the base circumference 11a, to protect it from accidental activation. For example, as shown in FIG. 10, the micro-switch 37 is positioned below the insertion niche 36 of the stethoscope, which prevents accidental pressing of the micro-switch, for example with the fingers.

The spring or button micro-switch 37 closes or opens the electric circuit depending on whether the device 1 is, respectively, coupled or decoupled to the stethoscope S. In certain embodiments, in addition to, or in place of, the switch described above, there may be a visible light and/or proximity sensor 35 (FIG. 7) connected to the command and control unit 4 to send a power-on command only if visible light is not detected in the cone 11 (light sensor) and/or if the proximity of the head of the stethoscope is not detected (proximity sensor). In fact, this would mean that the closure of the device 1 on the stethoscope S was not performed properly.

As mentioned previously, the coupling of the medical-healthcare device, in particular a stethoscope, to the sanitisation or sterilisation device 1 can take place by magnetic, mechanical or magneto-mechanical means. In the case of magnetic means, it is necessary that the stethoscope comprise ferromagnetic elements that can be attracted by the magnets present on the device of the invention.

If the stethoscope does not include ferromagnetic elements, this invention has a coupling system that provides for the positioning of additional ferromagnetic elements 27 (FIG. 6) on the stethoscope.

These ferromagnetic elements can be one or more ferromagnetic adhesive strips 27 of varying shape (bean, crescent, ring, tab, semicircle, etc.) that can be applied to the head T of the stethoscope S, on the surface opposite to the membrane to be sterilised.

In an embodiment, shown in FIGS. 5 and 6, there is provided a coupling member 20 to be positioned astride the connection nozzle 21 of the stethoscope with the tube 22 that leads to the earphones. The coupling member 20 comprises a U-shaped support 23 with ferromagnetic elements 24 positioned at the ends. The U-shaped support 23 comprises, always in proximity of the ends, two through holes 25, 25' aligned for the passage of a fastening pin 26, for example a fastening screw. The coupling member 20 is then placed astride the nozzle with the ferromagnetic elements 24 facing downwards so as to flank the surface to be sterilized and allow interaction with the magnets present on the device of the invention. The fastening pin 26, which will allow the stable coupling of the coupling member 20 to the stethoscope S is then inserted and screwed. If necessary in this embodiment too one or more ferromagnetic strips 27 can be applied on the upper surface 28 of the stethoscope.

In this way the stethoscope is provided with the necessary ferromagnetic elements that will allow magnetic coupling by attraction with the magnets of the device 1 of the invention.

The sanitisation or sterilisation device can be carried in a pocket. The particular shape of the case 2, which presents the cavity 9 dividing the bulk of the device into two portions (first and second chambers 6, 7) of an equivalent size in an embodiment (FIG. 1A) or with a chamber 7 longer than chamber 6 in another embodiment (FIG. 1B), allows optimising the portability of the device. In fact, the cavity 9 acts as a spring clip for fastening to a vest pocket of the white coat (or to a belt or a bag), so that the portion of the case 2 that contains the battery 5 and the command and control unit 4 remains inside the pocket, while the portion comprising the sanitisation or sterilisation means 3 and the cone 11 is positioned externally. It follows that the bulk of the projecting part is minimal and also the weight of the device is balanced between the two portions.

In a different embodiment, shown in FIG. 9, the device 1 is composed of two separate parts: a case 2', comprising the cone 11 with UV-C LED or LEDs 3, 3', 3", the command and control unit 4, and a support element 2" to which the battery 5 is associated.

As shown in the figure, the command and control unit 4 can also be divided between the case 2' and support element 2", having a first operating part 4', equipped for example with the electronic circuits for feeding and recharging the battery 5, in the support element 2", and a second operating part 4, equipped for example with the remaining electronic control circuits, inside the case 2'. The case 2' and the support element 2" comprise coupling means 30 for their mutual connection, such as an automatic button system or magnetic means. In this way, the device 1 can be disposed in any position of a white coat or other garment, without the need of a pocket or lapel, since the support element 2" will be positioned on the inner face of the fabric TS and the case 2' on the outer face, connecting the two parts through the fabric TS by the coupling means 30, snap or magnetic.

The support element 2" may comprise a lower portion 31, which can be part of the body of the battery 5, and which, positioned below with respect to the case 2', can counterbalance the weight of the latter.

The electrical connection between the battery 5 and the command and control unit 4 or between the battery 5 and element 4' from one side and the command and control unit 4 from the other side, can occur by means of a conductive pin system 32 that passes through the fabric TS.

The presence of the cone 11, on whose surface facing towards the interior of the chamber 6 the magnets 12 are arranged, allows coupling with stethoscopes even of different sizes. In fact, the magnetic coupling may take place along the whole surface of the cone 11, not necessarily only along the base circumference 11a. The same advantage can be achieved also in the case of mechanical coupling by replacing the ring nut 13 based on the shape and size of the stethoscope.

The sanitisation or sterilisation device 1 may be accompanied by a protective container (not shown). The protective container can be used when the device 1 is not used.

In general, the material of which device 1 is made is a material resistant to UV radiation, so as not to be deteriorated or damaged after a few uses by the operator, which can also occur in an inappropriate way.

The operation of the device 1 according to the invention is clear from what has been described above. After completing an examination, the medical-healthcare operator can couple the head of the stethoscope S to the device 1 in a simple and immediate way thanks to the magnetic, mechanical or even magnetic/mechanic coupling provided above.

At this point, the sanitisation/sterilisation cycle will be initiated manually or automatically and, when completed, the operator can decouple the device 1 from the stethoscope, which will be ready for a new use.

In certain embodiments, the device 1 can emit an acoustic, visual or vibratory signal to signal the end of the sanitisation/sterilisation cycle.

The battery can be charged wirelessly or by connection to the mains. In certain embodiments, the command and control unit 4 can regulate the power outputted by the UV-C LEDs 3, 3', 3" delivering more power if the device is connected to the mains, for example during the battery recharging phase, in order to fully sanitise or sterilise the medical device. Doing so will ensure sanitisation or sterilisation during the non-operational phase and, at the same, extend battery life.

The device of the invention can be wireless or Bluetooth-enabled to interface with electronic devices such as smartphones, tablets, computers and networks of information systems. This in order to display information about the device, such as for example, checking the charge level of the battery, the ageing of the UV-C LED, the duration of the disinfection time, check dates, times and frequencies/daily numbers for the use of the device, record and verify a serial number of the device, download the data on storage media, transmit the data to servers or computerised control systems or check that the electronics are operating properly (system check-up).

In certain embodiments, the device of the invention may comprise a Bluetooth or RFID recognition system in order to customise the device. The RFID system can also be used as a security system by configuring it as a sticker to be placed on the stethoscope (head or tube), so that, when the stethoscope is coupled to the device of the invention, it will give consent for powering on the UV-C LEDs.

The advantages of the sanitisation or sterilisation device 1 according to the invention are obvious.

The device is of minimal weight and size and is portable.

Despite being associable and dissociable from the stethoscope with a single gesture, thanks to magnetic, or mechanical or magneto-mechanical means, it may nevertheless be completely separated from the stethoscope, thus avoiding both its contamination during use of the stethoscope on the patient and its being a hindrance for the operator.

The use of the UV-C LEDs 3, 3', 3" allows the miniaturisation of the device.

The provision of the cone 11 as waveguide ensures a complete and effective irradiation of the entire surface to sanitized quickly, perfectly compatible with the passage of examining one patient after another, even using a single UV-C LED. Taking into account that the latter is the element of greatest cost of the device, the possibility of using only a single LED to cover the entire surface ensures a substantial reduction of manufacturing costs, as well as a greater battery life.

The command and control unit 4 allows performing all operations completely automatically, since the duration and intensity of the sterilisation cycle is regulated by a microprocessor or microcontroller, providing, at the same time, safety for both the operator and the patient because the operation of the UV-C LED is inhibited if the device is not properly closed on stethoscope or opened before the completion of sanitisation or sterilisation.

It obvious that only several particular embodiments of the present invention have been described, to which an expert in the art will be able to make any necessary modifications for its adaptation to particular applications without, however, departing from the scope of protection of this invention as defined in the appended claims.

The invention claimed is:

1. A sanitization or sterilization device for a stethoscope comprising a case that accommodates sanitization or sterilization means, a command and control unit and a battery, said device comprising means for coupling to the stethoscope to be sanitized or sterilized, said coupling means being magnetic or electromagnetic coupling means, mechanical coupling means or a combination thereof, wherein said case presents to the outside a recess which forms an inverted cone, the base of which is open and substantially at the level of the outer surface of the case where a base circumference is formed, said sanitization or sterilization means being arranged in correspondence to said cone, wherein, from the base circumference of the cone, thin, low ribs with chamfered edges branch-off towards the center of the cone.

2. The device according to claim 1, wherein the case has in cross section a U-shape, so as to comprise a first chamber, which comprises said cone and said sanitization or sterilization means, and a second chamber, which comprises said command and control unit and said battery, said first and second chambers being joined on one side by a connecting portion, so that between the two chambers, externally to them, is formed a cavity in the form of a slot that constitutes a means for attachment to a garment.

3. The device according to claim 2, wherein on the surface of the cavity, there are one of more protuberances, fixed or sprung.

4. The device according to claim 1, wherein the oblique side of the section of the cone perpendicular to its base has an inclination comprised between 20° and 30° with respect to the plane of the base.

5. The device according to claim 1, wherein the surface of the cone facing the aperture is reflective.

6. The device according to claim 5, wherein said surface of the cone comprises a coating of photocatalytic titanium dioxide.

7. The device according to claim 1, wherein the sanitisation or sterilisation means comprise one or more UV-C LEDs that emit radiation with a wavelength between 255 and 300 nm, or about 280 nm.

8. The device according to claim 7, wherein the UV-C LEDs are arranged in one of the following geometries:
 a UV-C LED disposed at the apex of the cone, or
 three UV-C LEDs arranged or inserted along the walls of the cone in a configuration of an equilateral triangle along a circumference coaxial to the base circumference of the cone and whose projection on the base of the cone is placed at a distance from the base circumference of r/2 where r is the radius of the base circumference, or
 two UV-C LEDs arranged or inserted along the walls of the cone in an opposed position, or
 four or more UV-C LEDs arranged at the vertices of regular polygons.

9. The device according to claim 1, wherein the magnetic coupling means consist of one or more magnets or electromagnetic elements positioned on the inner surface of the first chamber of the case, in correspondence to the cone.

10. The device according to claim 9, wherein the magnets or electromagnetic elements comprise a plurality of tabs arranged longitudinally on the inner wall of the cone, or one or more transverse tabs, or even a single magnetic element in the shape of a ring, coaxial with respect to the base circumference of the cone.

11. The device according to claim 1, wherein the mechanical coupling means comprise a ring nut arranged in correspondence to the base circumference of the cone and comprising an inner surface on which is arranged a plurality of engagement members, such as spring balls, latch levers and the like, and optionally an insertion niche, and wherein optionally permanent magnets in the form of tabs, tiles or a continuous circle are arranged inside the body of the ring nut or on its inner or outer surface.

12. The device according to claim 11, wherein the ring is removable and has a thread that can be coupled with a threaded edge provided in correspondence to the base circumference of the cone, or a bayonet connection system.

13. The device according to claim 11, wherein the ring nut is solidly associated to the base circumference of the cone.

14. The device according to claim 1, wherein the sanitisation or sterilisation means are operatively connected to the command and control unit and the battery via suitable cabling, wherein said cabling is made to pass through the connecting portion between the first chamber and second chamber of the case.

15. The device according to claim 1, wherein the command and control unit comprises a microprocessor or a microcontroller also with Digital Signal Processing (DSP) functions and wherein the command and control unit performs the following functions:
 a) controls that the device is closed on the head of the stethoscope and sends a command of consent for the performance of steps b) and c);

b) commands and controls the powering on and off of the UV-C LEDs based on pre-set power-on times and power output;
c) checks for anomalies, such as a malfunction of the UV-C LED or LEDs and an insufficient charge of the battery.

16. The device according to claim 1, in which the chamber externally comprises an extension constituted by a flat surface, which presents advertising text, identifying data of the operator, a badge, a screen or other data.

17. The device according to claim 1, comprising a case and a support element separate from said case, in which the case comprises the cone with the UV-C LED or LEDs and the command and control unit or an operational part of it, and said support element includes the battery and optionally an operational part complementary to said command and control unit, wherein the case and the support element comprise coupling means for their mutual connection, and a conductive pin system for the electrical connection between the battery and command and control units.

18. The device according to claim 1, comprising a wireless configuration to interface with electronic devices such as smartphones, tablets, computers and networks of information systems and/or a wireless or RFID recognition/security system.

19. The device according to claim 18, wherein said RFID recognition/security system includes an adhesive receiving antenna to be placed on the stethoscope, so that, when the stethoscope is coupled to the device, it gives consent for the powering on of the UV-C LEDs.

20. The device according to claim 1, wherein the outer edge of the device comprises an insertion niche formed by a protuberance towards the inside, below which is placed a micro-switch for sending a consent signal for powering on the UV-C LEDs.

21. The device according to claim 1, wherein inside the cone is positioned a visible light and/or proximity sensor for sending a consent signal for powering on the UV-C LEDs.

22. A kit comprising a device, as defined in claim 1, and a coupling system with a stethoscope comprising ferromagnetic elements apt to be positioned on the head of the stethoscope, on the surface opposite to the membrane to be sterilised, said ferromagnetic elements comprising one or more adhesive ferromagnetic strips of varying shape, such as bean, crescent, ring, tab or semicircle.

23. The kit according to claim 22, comprising a coupling member positionable on the stethoscope in proximity of the head, wherein the coupling member comprises a U-shaped support, at the ends of which are positioned ferromagnetic elements, the U-shaped support comprising, near the ends, two through holes aligned for the passage of a fastening pin.

* * * * *